US008283508B2

(12) United States Patent
Abe et al.

(10) Patent No.: US 8,283,508 B2
(45) Date of Patent: Oct. 9, 2012

(54) METHOD FOR PRODUCING AROMATIC COMPOUND

(75) Inventors: Koji Abe, Yamaguchi (JP); Yoshihiro Ushigoe, Yamaguchi (JP); Yuichi Kotou, Yamaguchi (JP); Ken Ikuno, Yamaguchi (JP); Takashi Hosomi, Yamaguchi (JP); Toyoaki Ihara, Yamaguchi (JP)

(73) Assignee: Ube Industries, Ltd., Ube-shi (JP)

( * ) Notice: Subject to any disclaimer, the term of this patent is extended or adjusted under 35 U.S.C. 154(b) by 450 days.

(21) Appl. No.: 12/671,858

(22) PCT Filed: Aug. 1, 2008

(86) PCT No.: PCT/JP2008/063836
§ 371 (c)(1),
(2), (4) Date: Feb. 2, 2010

(87) PCT Pub. No.: WO2009/022551
PCT Pub. Date: Feb. 19, 2009

(65) Prior Publication Data
US 2011/0230694 A1    Sep. 22, 2011

(30) Foreign Application Priority Data

Aug. 10, 2007  (JP) ................................. 2007-209977
Aug. 10, 2007  (JP) ................................. 2007-209978

(51) Int. Cl.
*C07C 1/32*    (2006.01)
(52) U.S. Cl. ...................................... 585/469
(58) Field of Classification Search ................... 585/469
See application file for complete search history.

(56) References Cited

U.S. PATENT DOCUMENTS
2004/0158093 A1* 8/2004 Ueda et al. ................... 558/411

FOREIGN PATENT DOCUMENTS
JP    11 228454    8/1999
JP    2005 239595    9/2005

OTHER PUBLICATIONS

Bringmann, G. et al., "Synthesis and Antiprotozoal Activities of Simplified Analogs of Naphthylisoquinoline Alkaloids", European Journal of Medical Chemistry, vol. 43, No. 1, pp. 32-42 (2008).
Zhang, A. et al., "Synthesis of Aminothiazole Derived Morphinans", Tetrahedron Letters, vol. 44, No. 34, pp. 6459-6462 (2003).
Bringmann, G. et al., "Biosynthesis of Naphthylisoquinoline Alkaloids: Synthesis and Incorporation of an Advanced $^{13}C2$-Labeled Isoquinoline Precursor", Tetrahedron, vol. 63, No. 8, pp. 1755-1761(2007).
England, D. B. et al., "Synthesis and Cross-Coupling Reactions of Substituted 5-Triflyloxyindoles", Journal of Organic Chemistry, vol. 70, No. 16, pp. 6519-6522, (2005).
Jackson, S. K. et al., "Total Synthesis of (±)-Herbindole A, (±)-Herbindole B, and (±)-Cis-Trikentrin A", Journal of Organic Chemistry, vol. 72, No. 4, pp. 1405-1411 (Jan. 8, 2007).
Sajiki, H. et al., "Pd/C-Catalyzed Deoxygenation of Phenol Derivatives Using Mg Metal and MeOH in the Presence of NH4OAc", Organic Letters, vol. 8, No. 5, p. 987-990 (2006).
Mori, A. et al., "Palladium on Carbon-Diethylamine-Mediated Hydrodeoxygenation of Phenol Derivatives under mild conditions", Tetrahedron, vol. 63, No. 5, pp. 1270-1280 (Jan. 29, 2007).

* cited by examiner

*Primary Examiner* — Thuan D Dang
(74) *Attorney, Agent, or Firm* — Oblon, Spivak, McClelland, Maier & Neustadt, L.L.P.

(57) ABSTRACT

The present invention is a method for producing an aromatic compound by substituting the sulfonic acid group in a sulfonic acid aromatic-ester with a hydrogen atom in the presence of a platinum group metal catalyst, wherein an alkali metal carboxylate and/or an ammonium formate are made to coexist in the system. According to the present invention, an aromatic compound where the sulfonic acid group in a sulfonic acid aromatic-ester is substituted with a hydrogen atom, can be produced efficiently with good operability without using metal magnesium.

7 Claims, No Drawings

METHOD FOR PRODUCING AROMATIC COMPOUND

TECHNICAL FIELD

The present invention relates to a method for producing an aromatic compound, comprising substituting the sulfonic acid group in a sulfonic acid aromatic-ester with a hydrogen atom in the presence of a platinum group metal catalyst.

BACKGROUND ART

Heretofore, as a method for producing an aromatic compound by substituting the sulfonic acid group in a sulfonic acid aromatic-ester with a hydrogen atom, known is a method of substituting the sulfonic acid group in a trifluoromethanesulfonate with a hydrogen atom by reacting a trifluoromethanesulfonate with magnesium in the presence of a platinum group metal (see Patent Reference 1 and Non-Patent Reference 1).

However, the method requires metal magnesium in an amount of not smaller than the equimolar amount of the sulfonate and metal magnesium does not dissolve in the reaction liquid, and therefore the method has some problems in that the operability is poor, the reaction control is difficult and the sulfonate concentration could not be increased. In addition, there is a possibility that the inner wall of the reactor may be damaged by metal magnesium and the plumbing may be clogged. Further, according to the method, in case where the alkyl moiety in the sulfonic acid group is an electron-deficient group such as a trifluoromethanesulfonic acid group, it is known that the ester is hydrolyzed and the reaction yield could not increase (see Non-Patent Reference 2, p. 1270).

In addition, Non-Patent Reference 2 discloses, as a method for producing an aromatic compound by substituting the sulfonic acid group in a sulfonic acid aromatic-ester with a hydrogen in the presence of a platinum group metal not using metal magnesium, a method of using a hydrogen gas and an amine compound such as diethylamine as a reducing agent.

However, according to the method, it is shown that, in a sulfonic acid aromatic-ester where three methoxy groups that are electron-donating groups substitute on the aromatic group, the sulfonic acid group such as a methanesulfonic acid group could not almost substituted with a hydrogen atom, and it is shown that the sulfonic acid group to which the method is applicable is limited only to an electron-deficient group such as a trifluoromethanesulfonic acid group. In addition, in the method, a hydrogen gas is used and therefore devices of a hydrogen cylinder, a regulator, a flow meter and the like are necessary, which require strict safety control.

[Patent Reference 1] JP-A 2005-239595
[Non-Patent Reference 1] Sajiki, H., et al.; Organic Letters, 2006, 8, 5, 987
[Non-Patent Reference 2] Mori, A., et al.; Tetrahedron, 2006, 63, 1270

DISCLOSURE OF THE INVENTION

An object of the present invention is to provide a method for producing an aromatic compound where the sulfonic acid group in a sulfonic acid aromatic-ester is substituted with a hydrogen atom, efficiently with good operability without using metal magnesium.

The present inventors have found that, in the conventional method for producing an aromatic compound by substituting the sulfonic acid group in a sulfonic acid aromatic-ester with a hydrogen atom, the above-mentioned problems can be solved by making an alkali metal carboxylate and/or an ammonium formate coexist in the system, and have completed the present invention.

Specifically, the present invention provides a method for producing an aromatic compound by substituting the sulfonic acid group in a sulfonic acid aromatic-ester with a hydrogen atom in the presence of a platinum group metal catalyst, wherein an alkali metal carboxylate and/or an ammonium formate are made to coexist in the system.

According to the present invention, an aromatic compound where the sulfonic acid group in a sulfonic acid aromatic-ester is substituted with a hydrogen atom can be produced with good operability and high efficiency, not using metal magnesium required by the conventional method. In addition, the concentration of the sulfonic acid aromatic-ester may be high therein, and therefore the method is excellent in producibility.

BEST MODE FOR CARRYING OUT THE INVENTION

The production method for an aromatic compound of the present invention is a method for producing an aromatic compound by substituting the sulfonic acid group in a sulfonic acid aromatic-ester with a hydrogen atom in the presence of a platinum group metal catalyst, wherein an alkali metal carboxylate and/or an ammonium formate are made to coexist in the system.

The ingredients for use in the present invention, the reaction conditions and others are described below.
(Sulfonic Acid Aromatic-Ester)

The sulfonic acid group in the sulfonic acid aromatic-ester to be used in the present invention is preferably a linear or branched alkanesulfonic acid group or an arylsulfonic acid group.

The alkanesulfonic acid group is preferably an alkanesulfonic acid group having from 1 to 5 carbon atoms, and the sulfonic acid group may be substituted by at least one halogen atom. The halogen atom is preferably a fluorine atom.

Specific examples of the alkanesulfonic acid group include a methanesulfonic acid group, an ethanesulfonic acid group, a propanesulfonic acid group, a butanesulfonic acid group, a pentanesulfonic acid group, a chloromethanesulfonic acid group, a trichloromethanesulfonic acid group, a fluoromethanesulfonic acid group, a difluoromethanesulfonic acid group, a trifluoromethanesulfonic acid group, a trifluoroethanesulfonic acid group, a pentafluoroethanesulfonic acid group, etc. Of those, preferred are alkanesulfonic acid groups having from 1 to 3 carbon atoms, and more preferred are a methanesulfonic acid group and an ethanesulfonic acid group.

The arylsulfonic acid group is preferably an arylsulfonic acid group having from 6 to 12 carbon atoms, and the sulfonic acid group may be substituted with at least one halogen atom. The halogen atom is preferably a fluorine atom.

Specific examples of the arylsulfonic acid group include a benzenesulfonic acid group, a toluenesulfonic acid group, an ethylbenzenesulfonic acid group, a trimethylbenzenesulfonic acid group, a triisopropylbenzenesulfonic acid group, etc. Preferred are a benzenesulfonic acid group and a toluenesulfonic acid group.

The sulfonic acid aromatic-ester for use in the present invention may be a compound having a substituent in addition to the sulfonic acid group. The other substituent than sulfonic acid group preferably substitutes on the aromatic ring of the sulfonic acid aromatic-ester, and the number of the substituent is at least one, preferably at least 2, and more preferably 3.

The other substituent than sulfonic acid group includes a linear or branched alkyl group having from 1 to 6 carbon atoms, an alkoxy group having from 1 to 4 carbon atoms. Concretely, it includes an alkyl group having from 1 to 4 carbon atoms such as a methyl group, an ethyl group, an isopropyl group, a tert-butyl group; and an alkoxy group having from 1 to 3 carbon atoms such as a methoxy group, ethoxy group; and more preferred is an alkyl group having from 1 to 4 carbon atoms such as a methyl group, an ethyl group, an isopropyl group, a tert-butyl group; even more preferred is a tert-butyl group.

Specific examples of the sulfonic acid aromatic-ester, in which the position for substitution with an alkyl group on the benzene ring is not specifically defined, include 2,4-di-tert-butylphenyl methanesulfonate, 2,4-di-tert-butylphenyl ethanesulfonate, 2,4-di-tert-butylphenyl propanesulfonate, 2,4-di-tert-butylphenyl butanesulfonate, 2,4-di-tert-butylphenyl fluoromethanesulfonate 2,4-di-tert-butylphenyl difluoromethanesulfonate, 2,4-di-tert-butylphenyl trifluoromethanesulfonate, 2,4-di-tert-butylphenyl pentafluoroethanesulfonate, 2,4-di-tert-butylphenyl trichloromethanesulfonate, 2,4-di-tert-butylphenyl benzenesulfonate, 2,4-di-tert-butylphenyl p-toluenesulfonate, 2,5-di-tert-butylphenyl methanesulfonate, 2,6-di-tert-butylphenyl methanesulfonate, 3,5-di-tert-butylphenyl methanesulfonate, 2,6-di-tert-butylphenyl trifluoromethanesulfonate, 3,5-di-tert-butylphenyl trifluoromethanesulfonate, 2,4,6-trimethylphenyl methanesulfonate, 2,4,6-triethylphenyl methanesulfonate, 2,4,6-tri-tert-butylphenyl methanesulfonate, 2,4-di-isopropylphenyl methanesulfonate, 2,6-di-isopropylphenyl methanesulfonate, 2,4,6-tri-isopropylphenyl methanesulfonate, 2,4-dimethoxyphenyl methanesulfonate, 2,6-dimethoxyphenyl methanesulfonate, 3,4-dimethoxyphenyl methanesulfonate, 2,4,6-trimethoxyphenyl methanesulfonate, 3,4,5-trimethoxyphenyl methanesulfonate, etc.

Of those, preferred are sulfonic acid aromatic-esters having, in addition to the sulfonic acid group, at least two substituents on the aromatic ring, such as 2,4-di-tert-butylphenyl methanesulfonate, 2,4-di-tert-butylphenyl ethanesulfonate, 2,4-di-tert-butylphenyl trifluoromethanesulfonate, 2,4-di-tert-butylphenyl trichloromethanesulfonate, 2,6-di-tert-butylphenyl methanesulfonate, 2,6-di-tert-butylphenyl trifluoromethanesulfonate, 3,5-di-tert-butylphenyl methanesulfonate, 2,4-di-isopropylphenyl methanesulfonate, 2,6-di-isopropylphenyl methanesulfonate, 2,4,6-tri-isopropylphenyl methanesulfonate, 2,4,6-trimethylphenyl methanesulfonate, 2,4,6-tri-tert-butylphenyl methanesulfonate, 3,4,5-trimethoxyphenyl methanesulfonate; and more preferred are sulfonic acid aromatic-esters having at least two, in total, of an alkyl group having from 1 to 4 carbon atoms and/or an alkoxy group having from 1 to 3 carbon atoms on the aromatic ring.

Even more preferred sulfonic acid aromatic-esters are compounds having, in addition to the sulfonic acid group, three substituents on the aromatic ring, such as 2,4,6-trimethylphenyl methanesulfonate, 2,4,6-tri-tert-butylphenyl methanesulfonate, 2,4,6-tri-isopropylphenyl methanesulfonate, 3,4,5-trimethoxyphenyl methanesulfonate; and still more preferred are compounds having three, in total, of an alkyl group having from 1 to 4 carbon atoms and/or an alkoxy group having from 1 to 3 carbon atoms on the aromatic ring.

However, the sulfonic acid aromatic-ester in the present invention is not limited to compounds having those substituents.

One or more of the above-mentioned sulfonic acid aromatic-esters can be used either singly or as combined.

(Solvent)

The solvent for use in the present invention includes alcohols having from 1 to 5 carbon atoms such as methanol, ethanol, 1-propanol, 2-propanol, n-butanol, tert-butanol; ethers such as tetrahydrofuran (THF), methyltetrahydrofuran, tetrahydropyran, dioxane; nitriles such as acetonitrile, propionitrile; carboxylic acids such as formic acid, acetic acid, etc. Of those, preferred are the solvents in which the solubility of sodium formate, lithium carboxylate, ammonium formate and sulfonic acid aromatic-esters is high. From that viewpoint, preferred are lower alcohols having from 1 to 3 carbon atoms, acetonitrile, THF; and especially preferred is methanol.

One or more these solvents may be used either singly or as combined.

Concretely, preferred combinations with the solvent include (i) a combination of a lower alcohol and formic acid, (ii) a combination of a lower alcohol and acetic acid, (iii) a combination of a lower alcohol, formic acid and acetic acid, (iv) a combination of a lower alcohol and water, (v) a combination of a lower alcohol and aqueous ammonia, (vi) a combination of a lower alcohol and an aqueous sodium hydroxide solution, etc. More preferred embodiments are (i) a combination of a lower alcohol and formic acid, (ii) a combination of a lower alcohol and acetic acid, (v) a combination of a lower alcohol and aqueous ammonia, etc.

In case where a lower alcohol such as methanol is used, as mixed with any other solvent, and when the proportion of the lower alcohol such as methanol is less than 50% by mass, then the solubility of the reaction substrate, sulfonic acid aromatic-ester in the mixed solvent may be low and the producibility may be thereby lowered. Accordingly, the ratio by mass of (lower alcohol/other solvent) is preferably from 99/1 to 50/50, more preferably from 98/2 to 70/30, even more preferably from 95/5 to 80/20.

The amount of the solvent to be used may be generally within a range of from 0.1 to 20 parts by mass relative to 1 part by mass of the sulfonic acid aromatic-ester, preferably from 0.5 to 15 parts by mass, more preferably from 1 to 10 parts by mass.

In the present invention, water, if any, may not interfere with the reaction; however, when water accounts for more than 30 parts by mass relative to 100 parts by mass of the total amount of the solvent, then the solubility of the reaction substrate, sulfonic acid aromatic-ester in the solvent may lower. Accordingly, the amount of water is preferably from 0 to 30 parts by mass relative to 100 parts by mass of the total amount of the solvent, more preferably from 0 to 20 parts by mass.

(Platinum Group Metal Catalyst)

The platinum group metal of the platinum group metal catalyst includes palladium, platinum, rhodium, iridium, ruthenium, etc. Of those, preferred are palladium and platinum; and more preferred is palladium as its reaction activity is the highest.

The platinum group metal catalyst may be a platinum group metal elementary substance as it is, such as palladium-black (black powdery palladium) and platinum-black (black powdery platinum), etc.; however, for enhancing the function of the catalyst, the metal may be supported by a porous carrier having a specific surface area of from 0.1 to 5000 $m^2/g$.

Preferred porous carriers include carbon (including activated carbon) having a specific surface area of from 500 to 3000 $m^2/g$, preferably from 600 to 2000 $m^2/g$; zeolite having a specific surface area of from 120 to 950 $m^2/g$, preferably from 150 to 800 m²/g; silica having a specific surface area of from 80 to 750 m²/g, preferably from 100 to 700 m²/g; silica-alumina having a specific surface area of from 65 to 650 m²/g, preferably from 100 to 550 m²/g; alumina having a specific surface area of from 30 to 350 m²/g, preferably from 50 to 300 m²/g; polymer having a specific surface area of from 150 to 250 m²/g, preferably from 160 to 240 m²/g; diatomaceous earth having a specific surface area of from 5 to 170 m²/g, preferably from 10 to 150 m²/g; magnesium salts, barium salts, calcium salts, etc.

When supported by such a porous carrier, the platinum group metal catalyst may be finely dispersed therein and is advantageous in that its catalytic function is thereby enhanced. Of those, more preferred are carbon, zeolite, silica, silica-alumina, alumina; and even more preferred is carbon.

When the amount of the supported platinum group metal catalyst is smaller than 0.1% by mass, then the catalyst activity may be poor; but more than 20% by mass may increase the cost unfavorably. Accordingly, the amount of the platinum group metal catalyst to be supported is preferably from 0.1 to 20% by mas, more preferably from 0.5 to 10% by mass, most preferably from 1 to 5% by mass as securing high dispersion.

When the amount of the platinum group metal catalyst to be used is smaller than 0.01 parts by mass, in terms of the platinum group metal therein, then relative to 100 parts by mass of the sulfonic acid aromatic-ester, then the reaction speed may be slow and the conversion of the sulfonic acid aromatic-ester may be low; but on the other hand, more than 10 parts by mass may increase the cost unfavorably since the platinum group metal catalyst is expensive. Accordingly, the amount of the platinum group metal catalyst to be used is preferably from 0.01 to 10 parts by mass, in terms of the platinum group metal therein, relative to 100 parts by mass of the sulfonic acid aromatic-catalyst, more preferably from 0.02 to 5 parts by mass, even more preferably from 0.05 to 2 parts by mass.

(Alkali Metal Carboxylate)

The alkali metal of the alkali metal carboxylate for use in the present invention includes lithium, sodium, potassium, etc. Of those, preferred is a lithium carboxylate compound as its solubility inorganic solvents, especially in alcohols is high.

Specific examples of the alkali metal carboxylate, in which the alkali metal is lithium, includes lithium formate, lithium acetate, lithium propionate, lithium oxalate, lithium succinate, lithium adipate, etc.

Where the alkali metal is sodium, they include sodium formate, sodium acetate, sodium propionate, sodium oxalate, sodium succinate, sodium adipate, etc.

Where the alkali metal is potassium, they include potassium formate, potassium acetate, potassium propionate, potassium oxalate, potassium succinate, potassium adipate, etc.

Of those, especially preferred is at least one selected from sodium formate, lithium formate, lithium acetate, lithium oxalate and potassium formate.

Regarding the amount of the alkali metal carboxylate such as sodium formate to be used, when the amount is smaller than 0.5 mols relative to 1 mol of the sulfonic acid aromatic-ester, then the reaction could not finish; but when more than 5 mols, then the solubility of the alkali metal carboxylate in the solvent may lower. Accordingly, the amount of the alkali metal carboxylate to be used is preferably from 0.5 to 5 mols relative to 1 mol of the sulfonic acid aromatic-ester, more preferably from 0.8 to 3 mols, even more preferably from 1 to 2 mols.

One or more the above-mentioned alkali metal carboxylates may be used either singly or as combined.

In use of the alkali metal carboxylate, a carboxylic acid and an alkali metal compound may be mixed in the reaction liquid since they may produce a compound that is chemically the same as the alkali metal carboxylate, therefore attaining the same effect as in the present invention. This method is also one embodiment of the present invention.

Concretely, the alkali metal carboxylate may be produced in the system, as in the following reaction formulae (1) to (7), therefore attaining the effect of the present invention.

In the exemplifications of the following reaction formulae, a monocarboxylic acid is used, in which, however, a di- or tri-carboxylic acid may also be used to produce the corresponding alkali metal carboxylate. In place of the carboxylic acid, for example, an ammonium carboxylate capable of being converted into an alkali metal carboxylate in the system may also be used to attain the same effect as that of the present invention. The present invention is not limited at all to these exemplifications, and any method capable of producing an alkali metal carboxylate through known technology is applicable thereto.

  (1)

  (2)

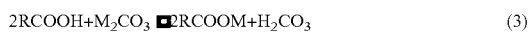  (3)

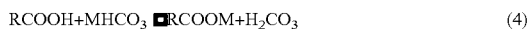  (4)

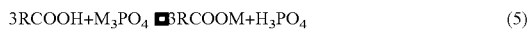  (5)

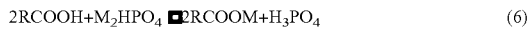  (6)

  (7)

(In the above formulae, R represents a hydrogen atom, or an alkyl group having from 1 to 5 carbon atoms, preferably from 1 to 3 carbon atoms; M represents lithium (Li), sodium (Na) or potassium (K); X represents fluorine (F), chlorine (Cl), bromine (Br) or iodine (I).)

Concretely, the carboxylic acid includes formic acid, acetic acid, propionic acid, oxalic acid, succinic acid, adipic acid, etc.; and preferred are formic acid, acetic acid and oxalic acid.

Concretely, the alkali metal compound includes oxides such as lithium oxide, sodium oxide, potassium oxide; alkali metal hydroxides such as lithium hydroxide, sodium hydroxide, potassium hydroxide; alkali metal carbonates such as lithium carbonate, sodium carbonate, potassium carbonate, lithium hydrogencarbonate, sodium hydrogencarbonate, potassium hydrogencarbonate; phosphates such as lithium phosphate, lithium hydrogenphosphate, sodium phosphate, sodium hydrogenphosphate, potassium phosphate, potassium hydrogenphosphate; alkali metal halides such as lithium fluoride, sodium fluoride, potassium fluoride, lithium chloride, sodium chloride, potassium chloride, lithium bromide, sodium bromide, potassium bromide, lithium iodide, sodium iodide, potassium iodide, etc. Of those preferred are lithium compounds such as lithium hydroxide, lithium carbonate, lithium fluoride and lithium chloride, as their solubility in alcohols such as methanol is high therefore their reactivity is high.

Regarding the combination of the carboxylic acid and the alkali metal compound, they may be combined each singly, or may be combined as two or more their mixtures.

Concrete combinations include a combination of formic acid and lithium hydroxide, a combination of formic acid and lithium carbonate, a combination of formic acid and lithium chloride, a combination of acetic acid and lithium hydroxide, a combination of acetic acid and lithium carbonate, a combination of acetic acid and lithium chloride, a combination of oxalic acid and lithium hydroxide, a combination of oxalic acid and lithium carbonate, a combination of oxalic acid and lithium chloride, etc.

Of those, more preferred are a combination of formic acid and sodium hydroxide, a combination of formic acid and sodium carbonate and a combination of formic acid and sodium chloride capable of producing sodium formate in the reaction liquid, and a combination of formic acid and lithium hydroxide, a combination of formic acid and lithium carbonate and a combination of formic acid and lithium chloride capable of producing lithium formate in the reaction liquid, since the solubility and the reactivity of the salt to be produced by mixing them could be high.

(Ammonium Formate)

Regarding the amount of ammonium formate to be used in the present invention, when the amount is smaller than 0.5 mols relative to 1 mol of the sulfonic acid aromatic-ester, then the reaction could not finish; but when more than 5 mols, then the solubility of ammonium formate in the solvent may lower. Accordingly, the amount of ammonium formate to be used is preferably from 0.5 to 5 mols relative to 1 mol of the sulfonic acid aromatic-ester, more preferably from 0.8 to 3 mols, even more preferably from 1 to 2 mols.

Ammonium formate may be used together with the alkali metal carboxylate; and regarding the amount thereof to be used in that case, when the amount is smaller than 0.5 mols relative to 1 mol of the sulfonic acid aromatic-ester, then the reaction could not finish; but when more than 5 mols, then the solubility of ammonium formate in the solvent may lower. Accordingly, the amount to be used is preferably from 0.5 to 5 mols each relative to 1 mol of the sulfonic acid aromatic-ester, more preferably from 0.8 to 3 mols, even more preferably from 1 to 2 mols.

(Other Ingredients)

In the present invention, an ammonium carboxylate may be further added to the system where an alkali metal carboxylate and/or ammonium formate co-exist therein. The ammonium carboxylate that may be added includes ammonium acetate, ammonium oxalate, etc.; and preferred is ammonium acetate.

The amount of the additional ammonium carbonate is preferably from 0.5 to 5 mols, more preferably from 1 to 2 mols relative to 1 mol of the sulfonic acid aromatic-ester.

(Reaction Condition)

The reaction in the present invention may be attained in a nitrogen atmosphere, an air atmosphere or a hydrogen atmosphere.

The lowermost limit of the reaction pressure in the reaction of the present invention may be generally at least 0.1 atmospheres (at least 10 kPa), preferably at least 0.5 atmospheres (at least 51 kPa). The lowermost limit of the pressure varies depending on the vapor pressure of the solvent to be used, but is preferably so controlled that the reaction mixture can maintain the boiling state thereof under the controlled pressure. The uppermost limit of the reaction pressure may be generally at most 10 atmospheres (at most 1013 kPa), preferably at most 5 atmospheres (at most 507 kPa). More concretely, in case where the reaction temperature is set to be higher than the boiling point of the reaction substance and the solvent, the pressure is preferably so controlled that the reaction temperature could rapidly reach the predetermined level thereof under the controlled pressure.

When the reaction temperature in the present invention is lower than −20° C., then the reaction speed may be too slow and the reaction may take a long time until its completion; but when higher than 250° C., then some side reaction may occur and the product may be readily degraded. Accordingly, the lowermost limit of the reaction temperature is preferably not lower than −20° C., more preferably not lower than 0° C.; and the uppermost limit of the reaction temperature is preferably not higher than 250° C., more preferably not higher than 150° C.

The preferred reaction time varies depending on the reaction temperature and on the amount to be used of the starting material, the platinum group metal catalyst, the alkali metal carboxylate and/or ammonium carboxylate, and the solvent; however, the lowermost limit of the time may be generally not shorter than 0.5 hours, preferably not shorter than 1 hour, and the uppermost limit thereof may be generally not longer than 24 hours, preferably not longer than 12 hours, from the viewpoint of the reaction efficiency.

The method of the present invention is especially effective in producing an aromatic compound into which multiple substituents are difficult to position-selectively introduce; and for the method, preferred are aromatic compounds having at least two substituents in addition to the sulfonic acid group, and most preferred are aromatic compounds having at least three substituents.

Concrete aromatic compounds include 1,3-di-tert-butylbenzene, 1,4-di-tert-butylbenzene, 1,3,5-tri-tert-butylbenzene, 1,3,5-trimethylbenzene, 1,3,5-triethylbenzene, 1,2-dimethoxybenzene, 1,3-dimethoxybenzene, 1,4-dimethoxybenzene, 1,2,3-trimethoxybenzene, 1,3,5-trimethoxybenzene, etc.; however, the present invention is not limited at all to these compounds.

(Regeneration of Catalyst)

In the present invention, the platinum group metal catalyst is collected through filtration from the reaction liquid after the reaction, and then dipped in an aqueous acidic solution selected from an aqueous hydrochloric acid solution, an aqueous acetic acid solution, an aqueous nitric acid solution and an aqueous formic acid solution, or in an aqueous alkaline solution such as an aqueous ammonia solution or the like to thereby regenerate the catalyst activity. Of those, an aqueous hydrochloric acid solution, an aqueous acetic acid solution and an aqueous ammonia solution are especially preferred as their regeneration effect is high.

The proportion of the above-mentioned aqueous solution to be used for catalyst regeneration is not specifically defined; however, when the proportion is less than 1 part by mass relative to 1 part by mass of the platinum group metal catalyst, then the regeneration effect may be low, but when more than 100 parts by mass, then it is insufficient since the producibility is low. Accordingly, the proportion of the aqueous solution is preferably from 1 to 100 parts by mass relative to 1 part by mass of the platinum group metal catalyst, more preferably from 1 to 50 parts by mass, most preferably from 5 to 50 parts by mass.

EXAMPLES

Examples of the present invention are shown below, by which, however, the present invention should not be limited.

Example I-1

In a nitrogen atmosphere, 2,4-di-tert-butylphenyl methanesulfonate (500 g, 1.76 mols), sodium formate (239 g, 3.52 mols), methanol (2400 g) and water (600 g) were mixed at 25° C., and with stirring, 10 mass % Pd/carbon (50 mass water-containing product) (30 g) (as metal palladium; 0.3 mass % relative to 2,4-di-tert-butylphenyl methanesulfonate) as supported by a carbon carrier having a specific surface area of 780 m$^2$/g (by BET method) was put into it. Still kept stirred, this was heated up to 65° C., taking 1 hour, and reacted for 6 hours. Water (100 mL) was added to the reaction liquid and Pd-carbon was separated through filtration, then heptane (500 g) was added to the filtrate. The organic layer obtained after extraction was concentrated under reduced pressure to give crude 1,3-di-tert-butylbenzene (331 g, yield 99% by mass). The result is shown in Table I-1.

Example I-2

The same reaction as in Example I-1 was carried out, except that sodium formate was used in an amount of 1.5 molar times relative to 2,4-di-tert-butylphenyl methanesulfonate. The result is shown in Table I-1.

Example I-3

The same reaction as in Example I-1 was carried out, except that sodium formate was used in an amount of 3 molar times relative to 2,4-di-tert-butylphenyl methanesulfonate. The result is shown in Table I-1.

Comparative Example I-1

The same reaction as in Example I-1 was carried out for 10 hours, except that the alkali metal carboxylate was not added but ammonium acetate was added as an ammonium carboxylate in an amount of 2 molar times relative to 2,4-di-tert-butylphenyl methanesulfonate. The result is shown in Table I-1.

Comparative Example I-2

In a nitrogen atmosphere under normal pressure, 2,4-di-tert-butylphenyl methanesulfonate (500 g, 1.76 mols), ammonium acetate (678 g, 8.79 mols) and methanol (3000 g) were mixed at 25° C., and with stirring, 10 mass % Pd/carbon (50 mass % water-containing product) (100 g) (as metal palladium; 1 mass % relative to 2,4-di-tert-butylphenyl methanesulfonate) as supported by a carbon carrier having a specific surface area of 780 m$^2$/g (by BET method) and powdery magnesium (60 g, 2.46 mols) were put into it. With stirring, the reaction liquid was reacted at the same temperature for 9 hours. Water (1000 mL) was added to the reaction liquid and Pd-carbon was separated through filtration, then heptane (1000 g) was added to the filtrate. The organic layer obtained after extraction was concentrated under reduced pressure to give crude 1,3-di-tert-butylbenzene (318 g, yield 95% by mass). The result is shown in Table I-1.

Comparative Example I-3

The same reaction as in Example I-1 was carried out for 7 hours, except that, in a hydrogen atmosphere, the alkali metal carboxylate was not added but diethylamine was added in an amount of 1.2 molar times relative to 2,4-di-tert-butylphenyl methanesulfonate, and 10 mass % Pd/carbon (50 mass % water-containing product) was used in an amount of 100 g (as metal palladium; 1 mass % relative to 2,4-di-tert-butylphenyl methanesulfonate). The result is shown in Table I-1.

TABLE I-1

| | Co-existing Compound (molar ratio relative to sulfonic acid aromatic-ester) | Mg Addition | Reaction Atmosphere | Reaction Time (hr) | Reaction Yield (%) |
|---|---|---|---|---|---|
| Example I-1 | Sodium Formate (2) | no | nitrogen | 6 | 99 |
| Example I-2 | Sodium F)ormate (1.5) | no | nitrogen | 6 | 97 |
| Example I-3 | Sodium Formate (3) | no | nitrogen | 6 | 82 |
| Comparative Example I-1 | Ammonium Acetate (2) | no | nitrogen | 10 | 0 |
| Comparative Example I-2 | Ammonium Acetate (5) | yes | nitrogen | 9 | 95 |
| Comparative Example I-3 | Diethylamine (1.2) | no | hydrogen | 7 | 51 |

The numeral in the parenthesis indicates the molar ratio relative to the sulfonic acid aromatic-ester.

Example I-4

The same reaction as in Example I-1 was carried out for 6 hours, except that methanol was used as the solvent in place of methanol/water (ratio by mass, 8/2). The result is shown in Table I-2.

Example I-5

The same reaction as in Example I-1 was carried out for 6 hours, except that 1-butanol was used as the solvent in place of methanol/water (ratio by mass, 8/2). The result is shown in Table I-2.

Example I-6

The same reaction as in Example I-1 was carried out for 6 hours, except that methanol/formic acid (ratio by mass, 9/1) was used as the solvent in place of methanol/water (ratio by mass, 8/2). The result is shown in Table I-2.

Example I-7

The same reaction as in Example I-1 was carried out for 6 hours, except that methanol/acetic acid (ratio by mass, 9/1) was used as the solvent in place of methanol/water (ratio by mass, 8/2). The result is shown in Table I-2.

TABLE I-2

| | Solvent | Reaction Temperature (° C.) | Reaction Time (hr) | Reaction Yield (%) |
|---|---|---|---|---|
| Example I-1 | methanol/water (ratio by mass, 8/2) | 65 | 6 | 99 |
| Example I-4 | methanol | 65 | 6 | 95 |
| Example I-5 | 1-butanol | 65 | 6 | 92 |
| Example I-6 | methanol/formic acid (ratio by mass, 9/1) | 65 | 6 | 88 |
| Example I-7 | methanol/acetic acid (ratio by mass, 9/1) | 65 | 6 | 96 |

Example I-8

The reaction of Example I-1 was carried out under the same condition as in Example I-1, except that the reaction temperature was changed to 0° C.; and the reaction time was 24 hours, and the reaction yield was 80% by mass.

Example I-9

The reaction of Example I-1 was carried out under the same condition as in Example I-1, except that the reaction temperature was changed to 25° C.; and the reaction time was 9 hours, and the reaction yield was 84% by mass.

Example II-1

In a nitrogen atmosphere under normal pressure, 2,4-di-tert-butylphenyl methanesulfonate (500 g, 1.76 mols), lithium formate (183 g, 3.52 mols) and methanol (3000 g) were mixed at 25° C., and with stirring, 10 mass % Pd/carbon (50 mass % water-containing product) (100 g) (as metal palladium; 1 mass % relative to 2,4-di-tert-butylphenyl methanesulfonate) as supported by a carbon carrier having a specific surface area of 780 $m^2/g$ (by BET method) was put into it. With stirring, the reaction liquid was reacted at the same temperature for 4 hours. Water (100 mL) was added to the reaction liquid and Pd-carbon was separated through filtration, then heptane (500 g) was added to the filtrate. The organic layer obtained after extraction was concentrated under reduced pressure to give crude 1,3-di-tert-butylbenzene (334 g, yield 100% by mass).

Example II-2

The same reaction as in Example II-1 was carried out, except that potassium formate was used in place of lithium formate and the reaction time was changed to 7 hours. The result is shown in Table II-1.

Example II-3

The same reaction as in Example II-1 was carried out for 7 hours, except that the alkali metal carboxylate was not added but ammonium formate was added as an ammonium carboxylate in an amount of 2 molar times relative to 2,4-di-tert-butylphenyl methanesulfonate. The result is shown in Table II-1.

Comparative Example II-1

The same reaction as in Example II-1 was carried out for 10 hours, except that the alkali metal carboxylate was not added but ammonium acetate was added as an ammonium carboxylate in an amount of 2 molar times relative to 2,4-di-tert-butylphenyl methanesulfonate. The result is shown in Table II-1.

Example II-4

The same reaction as in Example II-1 was carried out, except that lithium formate was changed to lithium acetate, and that the alkali metal carboxylate was not added but ammonium formate as an ammonium carboxylate was added in an amount of 2 molar times relative to 2,4-di-tert-butylphenyl methanesulfonate. The result is shown in Table II-1.

Example II-5

The same reaction as in Example II-1 was carried out, except that lithium formate was changed to sodium acetate, and that the alkali metal carboxylate was not added but ammonium formate as an ammonium carboxylate was added in an amount of molar times relative to 2,4-di-tert-butylphenyl methanesulfonate. The result is shown in Table II-1.

Example II-6

The same reaction as in Example II-4 was carried out, except that 2 molar times of lithium formate was changed to 1 molar time of lithium oxalate. The result is shown in Table II-1.

Example II-7

The same reaction as in Example II-5 was carried out, except that 2 molar times of lithium formate was changed to 1 molar time of sodium oxalate. The result is shown in Table II-1.

TABLE II-1

|  | Sulfonic Acid Aromatic-Ester | Alkali Metal Carboxylate | Ammonium Carboxylate | Reaction Time (hr) | Reaction Yield (%) |
|---|---|---|---|---|---|
| Example II-1 | 2,4-di-tert-butylphenyl methanesulfonate | lithium formate (2) | no | 4 | 100 |
| Example II-2 | 2,4-di-tert-butylphenyl methanesulfonate | potassium formate (2) | no | 7 | 82 |
| Example II-3 | 2,4-di-tert-butylphenyl methanesulfonate | no | ammonium formate (2) | 7 | 84 |
| Comparative Example II-1 | 2,4-di-tert-butylphenyl methanesulfonate | no | ammonium acetate (2) | 10 | 0 |
| Example II-4 | 2,4-di-tert-butylphenyl methanesulfonate | lithium acetate (2) | ammonium formate (2) | 4 | 100 |
| Example II-5 | 2,4-di-tert-butylphenyl methanesulfonate | sodium acetate (2) | ammonium formate (2) | 4 | 100 |
| Example II-6 | 2,4-di-tert-butylphenyl methanesulfonate | lithium oxalate (1) | ammonium formate (2) | 4 | 100 |
| Example II-7 | 2,4-di-tert-butylphenyl methanesulfonate | sodium oxalate (1) | ammonium formate (2) | 4 | 100 |

The numeral in the parenthesis indicates the molar ratio relative to the sulfonic acid aromatic-ester.

Example II-8

In a nitrogen atmosphere under normal pressure, 2,4-di-tert-butylphenyl methanesulfonate (500 g, 1.76 mols), formic acid (162 g, 3.52 mols), lithium hydroxide (84 g, 3.52 mols) and methanol (3000 g) were mixed at 25° C., and with stirring, 10 mass % Pd/carbon (50 mass % water-containing product) (100 g) (as metal palladium; 1 mass % relative to 2,4-di-tert-butylphenyl methanesulfonate) as supported by a carbon carrier having a specific surface area of 780 m²/g (by BET method) was put into it. With stirring, the reaction liquid was reacted at the same temperature for 2 hours. Water (100 mL) was added to the reaction liquid and Pd-carbon was separated through filtration, then heptane (500 g) was added to the filtrate. The organic layer obtained after extraction was concentrated under reduced pressure to give crude 1,3-di-tert-butylbenzene (334 g, yield 100%, by mass). The result is shown in Table II-2.

Example II-9

In a nitrogen atmosphere under normal pressure, 2,4-di-tert-butylphenyl methanesulfonate (30 g, 0.11 mols), formic acid (9.7 g, 0.21 mols), lithium carbonate (7.8 g, 0.11 mols) and methanol (180 g) were mixed at 25° C., and with stirring, 10 mass % Pd/carbon (50 mass % water-containing product) (6 g) (as metal palladium; 1 mass % relative to 2,4-di-tert-butylphenyl methanesulfonate) as supported by a carbon carrier having a specific surface area of 780 m²/g (by BET method) was put into it. With stirring, the reaction liquid was reacted at the same temperature for 4 hours. Water (10 mL) was added to the reaction liquid and Pd-carbon was separated through filtration, then heptane (30 g) was added to the filtrate. The organic layer obtained after extraction was concentrated under reduced pressure to give crude 1,3-di-tert-butylbenzene (20 g, yield 100% by mass). The result is shown in Table II-2.

Example II-10

In a nitrogen atmosphere under normal pressure, 2,4-di-tert-butylphenyl methanesulfonate (30 g, 0.11 mols), formic acid (9.7 g, 0.21 mols), lithium chloride (8.9 g, 0.21 mols) and methanol (180 g) were mixed at 25° C., and with stirring, 10 mass % Pd/carbon (50 mass % water-containing product) (6 g) as supported by a carbon carrier having a specific surface area of 780 m²/g (by BET method) (as metal palladium; 1 mass relative to 2,4-di-tert-butylphenyl methanesulfonate) was put into it. With stirring, the reaction liquid was reacted at the same temperature for 9 hours. Water (10 mL) was added to the reaction liquid and Pd-carbon was separated through filtration, then heptane (30 g) was added to the filtrate. The organic layer obtained after extraction was concentrated under reduced pressure to give crude 1,3-di-tert-butylbenzene (16 g, yield 81% by mass). The result is shown in Table II-2.

TABLE II-2

| | Sulfonic Acid Aromatic-Ester | Carboxylic Acid | Alkali Metal Compound | Reaction Time (hr) | Reaction Yield (%) |
|---|---|---|---|---|---|
| Example II-8 | 2,4-di-tert-butylphenyl methanesulfonate | formic acid (2) | lithium hydroxide (2) | 4 | 100 |
| Example II-9 | 2,4-di-tert-butylphenyl methanesulfonate | formic acid (2) | lithium carbonate (1) | 4 | 100 |
| Example II-10 | 2,4-di-tert-butylphenyl methanesulfonate | formic acid (2) | lithium chloride (2) | 9 | 81 |

The numeral in the parenthesis indicates the molar ratio relative to the sulfonic acid aromatic-ester.

Example II-11

In a nitrogen atmosphere under normal pressure, 2,4-di-tert-butylphenyl methanesulfonate (30 g, 0.11 mols), ammonium formate (13.3 g, 0.21 mols), lithium chloride (8.9 g, 0.21 mols) and methanol (180 g) were mixed at 25° C., and with stirring, 10 mass % Pd/carbon (50 mass % water-containing product) (6 g) (as metal palladium; 1 mass % relative to 2,4-di-tert-butylphenyl methanesulfonate) as supported by a carbon carrier having a specific surface area of 780 m²/g (by BET method) was put into it. With stirring, the reaction liquid was reacted at the same temperature for 4 hours. Water (10 mL) was added to the reaction liquid and Pd-carbon was separated through filtration, then heptane (30 g) was added to the filtrate. The organic layer obtained after extraction was concentrated under reduced pressure to give crude 1,3-di-tert-butylbenzene (20 g, yield 100% by mass).

Example II-12

In a nitrogen atmosphere under normal pressure, 2,4-di-tert-butylphenyl methanesulfonate (30 g, 0.11 mols), ammonium formate (8.0 g, 0.13 mols), lithium acetate (8.4 g, 0.13 mols) and methanol (45 g) were mixed at 25° C., and with stirring, 10 mass % Pd/carbon (50 mass % water-containing product) (1.2 g) (as metal palladium; 0.2 mass % relative to 2,4-di-tert-butylphenyl methanesulfonate) as supported by a carbon carrier having a specific surface area of 780 m²/g (by BET method) was put into it. With stirring, the reaction liquid was reacted at the same temperature for 4 hours. Water (10 mL) was added to the reaction liquid and Pd-carbon was separated through filtration, then heptane (30 g) was added to the filtrate. The organic layer obtained after extraction was concentrated under reduced pressure to give crude 1,3-di-tert-butylbenzene (16 g, yield 81% by mass). The result is shown in Table II-3.

Example II-13

The same reaction as in Example II-12 was carried out, except that 2 mass % Pd/carbon (50 mass % water-containing product) was used in an amount of 6 g (as metal palladium; 0.2 mass % relative to 2,4-di-tert-butylphenyl methanesulfonate) as the catalyst. The result is shown in Table II-3.

Example II-14

The same reaction as in Example II-12 was carried out, except that 2 mass % Pd/carbon (50 mass % water-containing product) was used in an amount of 3 g (as metal palladium; 0.1 mass % relative to 2,4-di-tert-butylphenyl methanesulfonate) as the catalyst. The result is shown in Table II-3.

TABLE II-3

| Type of Catalyst | Amount of Catalyst Used (mass % relative to sulfonic acid aromatic-ester) [in terms of dry mass] | Reaction Time (hr) | Reaction Yield (%) |
| --- | --- | --- | --- |
| Example II-12 | 10% Pd/carbon | 2 | 4 | 81 |
| Example II-13 | 2% Pd/carbon | 10 | 4 | 91 |
| Example II-14 | 2% Pd/carbon | 5 | 4 | 83 |

Example II-15

The same reaction as in Example II-1 was carried out for 7 hours, except that methanol/water (ratio by mass, 8/2) was used as the solvent in place of methanol. The result is shown in Table II-4.

Example II-16

The same reaction as in Example II-1 was carried out for 7 hours, except that 1-butanol was used as the solvent in place of methanol. The result is shown in Table II-4.

Example II-17

The same reaction as in Example II-15 was carried out for 7 hours, except that methanol/formic acid (ratio by mass, 9/1) was used as the solvent in place of methanol/water (ratio by mass, 8/2). The result is shown in Table II-4.

Example II-18

The same reaction as in Example II-15 was carried out for 7 hours, except that methanol/acetic acid (ratio by mass, 9/1) was used as the solvent in place of methanol/water (ratio by mass, 8/2). The result is shown in Table II-4.

TABLE II-4

| | Solvent | Reaction Time (hr) | Reaction Yield (%) |
| --- | --- | --- | --- |
| Example II-1 | methanol | 4 | 100 |
| Example II-15 | methanol/water (ratio by mass, 8/2) | 7 | 100 |
| Example II-16 | 1-butanol | 7 | 97 |
| Example II-17 | methanol/formic acid (ratio by mass, 9/1) | 7 | 89 |
| Example II-18 | methanol/acetic acid (ratio by mass, 9/1) | 7 | 99 |

Reference Example 1

10 mass % Pd/carbon used in Example II-1 was collected from the reaction liquid through filtration, then washed with methanol/water (1/1, ratio by mass) (200 mL) and recovered. 10 g of the thus-obtained Pd-carbon was taken, dipped in aqueous 35% hydrochloric acid solution (130 g), and stirred at 25° C. for 1 hour. After thus stirred, this was heated at 60° C. to dryness under a reduced pressure of 10 Torr (1.3 kPa) to give regenerated Pd/carbon (10 g).

Using the thus-obtained, regenerated Pd/carbon (10 g), the same reaction as in Example II-1 was carried out in a nitrogen atmosphere under normal pressure at 25° C., in which, however, 2,4-di-tert-butylphenyl methanesulfonate (100 g, 0.35 mols), lithium formate (37 g, 0.70 mols) and methanol (600 g) were used. Water (20 mL) was added to the reaction liquid and Pd/carbon was collected through filtration, and heptane (100 g) was added to the filtrate. The organic layer obtained after extraction was concentrated under reduced pressure to give crude 1,3-di-tert-butylbenzene (50 g, yield 75% by mass).

INDUSTRIAL APPLICABILITY

According to the present invention, an aromatic compound where the sulfonic acid group in a sulfonic acid aromatic-ester is substituted with a hydrogen atom, can be produced efficiently with good operability.

The invention claimed is:

1. A method for producing an aromatic compound by substituting the sulfonic acid group in a sulfonic acid aromatic-ester with a hydrogen atom in the presence of a platinum group metal catalyst, wherein an alkali metal carboxylate and/or an ammonium formate are made to coexist in the reaction.

2. The method for producing an aromatic compound as claimed in claim 1, wherein the alkali metal carboxylate is at least one selected from sodium formate, lithium formate, lithium acetate, lithium oxalate and potassium formate.

3. The method for producing an aromatic compound as claimed in claim 1, wherein the platinum group metal catalyst contains palladium-black or platinum-black, and the amount of the platinum group metal catalyst to be used is from 0.01 to 10 parts by mass relative to 100 parts by mass of the sulfonic acid aromatic-ester.

4. The method for producing an aromatic compound as claimed in claim 1, wherein the amount of the alkali metal carboxylate and/or ammonium formate to be used is from 0.5 to 5 mols each relative to 1 mol of the sulfonic acid aromatic-ester.

5. The method for producing an aromatic compound as claimed in claim 1, wherein the sulfonic acid aromatic-ester is an aromatic compound having at least two substituents in addition to the sulfonic acid group.

6. The method for producing an aromatic compound as claimed in claim 5, wherein the substituent is a tert-butyl group.

7. The method for producing an aromatic compound as claimed in claim 1, wherein the sulfonic acid group is an alkanesulfonic acid group having from 1 to 5 carbon atoms, or an arylsulfonic acid group having from 6 to 12 carbon atoms.

* * * * *